United States Patent
Tachibana et al.

[11] Patent Number: 6,030,119
[45] Date of Patent: Feb. 29, 2000

[54] DENTAL X-RAY IMAGE DETECTING APPARATUS AND ADAPTOR FOR SAME

[75] Inventors: Akifumi Tachibana; Masakazu Suzuki; Hideki Yoshikawa; Susumu Kirimura, all of Kyoto; Tetsuhiko Muraki, Hamamatsu; Hitoshi Asai, Hamamatsu; Kazuhisa Miyaguchi, Hamamatsu, all of Japan

[73] Assignees: J. Morita Manufacturing Corporation, Kyoto; Hamamatsu Photonics Kabushiki Kaisha, Shizuoka, both of Japan

[21] Appl. No.: 09/049,740

[22] Filed: Mar. 27, 1998

[30] Foreign Application Priority Data

Apr. 8, 1997 [JP] Japan ................................ 9-089664

[51] Int. Cl.[7] ........................................................ G21K 4/00
[52] U.S. Cl. ............................ 378/169; 378/210; 378/191
[58] Field of Search .................... 378/169, 98.8, 378/168, 191; 250/370.09

[56] References Cited

U.S. PATENT DOCUMENTS 5,677,537  10/1997  Pfeiffer.
5,691,539  11/1997  Pfeiffer ...................................... 378/191
5,773,832   6/1998  Sayed et al..

FOREIGN PATENT DOCUMENTS 8-280669  10/1996  Japan.

*Primary Examiner*—Craig E. Church
*Attorney, Agent, or Firm*—Koda & Androlia

[57] ABSTRACT

An X-ray detecting element detects an image produced by X-ray irradiation. An apparatus case capable of being inserted into a mouth has an X-ray irradiation face having different dimensions in two directions perpendicular to each other, and houses the X-ray detecting element. A cable is connected to the apparatus case to transmit a signal from the X-ray detecting element to the outside of the apparatus case. The cable is drawn out from the apparatus case in a direction which is parallel with the X-ray irradiation face and perpendicular to the longitudinal direction of the X-ray irradiation face. According to this configuration, the cable does not obstruct the imaging operation in a course of imaging teeth in a mouth, particularly a molar portion. Therefore, an imaging operation can be easily conducted without giving the subject an unpleasant feeling.

6 Claims, 18 Drawing Sheets

DENTAL X-RAY IMAGE DETECTING APPARATUS AND ADAPTOR FOR SAME

BACKGROUND OF THE INVENTION

1. Field of the Invention

The present invention relates to a dental X-ray image detecting apparatus for taking mainly an X-ray image of an object having a relatively small area, such as teeth or the like, and also relates to an adaptor for the apparatus.

2. Description of the Related Art

FIG. 23A shows an X-ray image detecting apparatus 1 disclosed in Japanese unexamined patent publication JP-A 8-280669 (1996). The X-ray image detecting apparatus 1 comprises an X-ray detecting element 2, an apparatus case 3 for housing the element, and a cable 4 connected to the element. In the X-ray image detecting apparatus 1 shown in FIGS. 23A to 23C, the cable 4 is drawn out in the longitudinal direction of the apparatus case 3.

When an intraoral image is taken by using the X-ray image detecting apparatus 1, the longitudinal direction of the apparatus case 3 is set to be along with the direction in which teeth erect, i.e., the occulusal direction. Therefore, the cable 4 projects in the occulusal direction, and obstructs the positioning of the detecting apparatus in the interior of a mouth. When an imaging operation is conducted in an appropriate position while the cable 4 is projected in the occulusal direction, the subject to be diagnosed must open the mouth more largely than the longitudinal length of the apparatus case. This produces strain on the subject. Particularly in the case where a molar tooth portion should be imaged, even when the subject largely opens the mouth, the X-ray image detecting apparatus 1 may not be adequately positioned, whereby the imaging operation itself is impossible.

In the X-ray image detecting apparatus 1, since the cable 4 is connected and fixed to the apparatus case 3, the cable 4 is bent when a molar tooth portion is imaged, and the fixed portion is stressed, with the result that the inner conductors are easily broken. Since the cable 4 is integrated with the apparatus case 3, when the conductors of the cable 4 are once broken, the whole X-ray image detecting apparatus 1 must be replaced with another one. This is uneconomical.

JP-A 8-280669 also discloses another configuration of the detecting apparatus in which a face of the apparatus case 3 abutting against the imaging site is formed to be a curved face, and a soft resin is used as the material so that the detecting apparatus fits to an intraoral or dental arch shape. However, such a configuration cannot cope with different intraoral or dental arch shapes. In other words, intraoral and dental arch shapes are different not only between children and adults, but also between individual subjects. Furthermore, even in the same subject, the shapes of individual intraoral or dental arch portions are different. Therefore it is impossible to make the apparatus case 3 fit to all the intraoral or dental arch portions.

SUMMARY OF THE INVENTION

It is an object of the invention to provide a dental X-ray image detecting apparatus for easily taking an image without giving a subject an unpleasant feeling, and an adaptor for the apparatus.

In a first aspect of the invention, a dental X-ray image detecting apparatus comprises:

an X-ray detecting element for detecting an image produced by X-ray irradiation;

an apparatus case for housing the X-ray detecting element, including an X-ray irradiation face having different dimensions in two directions perpendicular to each other, the apparatus case being capable of being inserted into a mouth; and a cable connected to the X-ray detecting element, for transmitting a signal from the X-ray detecting element to an external apparatus, wherein the cable is drawn out in a direction which is perpendicular to a longitudinal direction of the X-ray irradiation face.

According to the first aspect of the invention, since the cable is drawn out in a direction perpendicular to the longitudinal direction of the X-ray irradiation face, the cable does not obstruct the positioning of the detecting apparatus in a mouth when an image of tooth, particularly a molar portion, is taken in the mouth. In this configuration, an imaging operation can be easily conducted without giving the subject an unpleasant feeling. In the course of imaging process, the cable is not projected in the occulusal direction, and the bending degree of the cable is relieved, with the result that the risk of breaking the cable can be decreased.

In a second aspect of the invention, a dental X-ray image detecting apparatus comprises:

an X-ray detecting element for detecting an image produced by X-ray irradiation;

an apparatus case for housing the X-ray detecting element, capable of being inserted into a mouth;

a cable connected to the X-ray detecting element for transmitting a signal from the X-ray detecting element to an external apparatus; and a cable attaching and detaching mechanism for attaching the cable to and detaching the cable from the X-ray detecting element.

According to the second aspect of the invention, the cable can be attached to and detached from the X-ray detecting element. When the cable is broken, therefore, only the cable can be easily replaced with another one without replacing other components which are not related to the breakage of the cable, such as the X-ray detecting element which normally operates, and the apparatus case which is not broken or stained. Accordingly, the X-ray image detecting apparatus is remarkably economical.

In a third aspect of the invention, the cable attaching and detaching mechanism have a watertight seal member.

According to the third aspect of the invention, when the cable is connected to the X-ray image detecting element, the seal member can prevent water from entering the apparatus. Consequently, saliva in the mouth does not enter the portion where the cable is connected to the apparatus case, thereby preventing a breakdown due to entry of water. Moreover, the entry of water can be prevented without using a disposable cover.

In a fourth aspect of the invention, a dental X-ray image detecting apparatus comprises:

an X-ray detecting element for detecting an image produced by X-ray irradiation;

an apparatus case for housing the X-ray detecting element, capable of being inserted into a mouth;

a cable connected to the X-ray detecting element, for transmitting a signal from the X-ray detecting element to an external apparatus; and a cable connecting mechanism for changing a draw-out direction of the cable and/or a draw-out position of the cable with respect to the X-ray detecting element.

According to the fourth aspect of the invention, the draw-out direction of the cable from the X-ray detecting element or the draw-out position of the cable can be changed. Therefore, the draw-out direction of the cable or the draw-out position of the cable can be selected so that the cable does not obstruct an imaging operation or the subject is not required to largely open the mouth. Consequently, an imaging operation can be easily conducted without giving the subject an unpleasant feeling.

In a fifth aspect of the invention, a dental X-ray image detecting apparatus comprises:

an X-ray detecting element for detecting an image produced by X-ray irradiation;

an apparatus case for housing the X-ray detecting element, capable of being inserted into a mouth;

first and second cables for transmitting a signal from the X-ray detecting element to an external apparatus; and first and second connectors disposed at ends of the first and second cables, respectively, which are selectively connected to the X-ray detecting element so as to differentiate a cable draw-out direction with respect to the X-ray detecting element.

According to the fifth aspect of the invention, the direction in which, when the first connector is connected to the X-ray detecting element, the first cable is drawn out with respect to the apparatus case, is different from that in which, when the second connector is connected to the X-ray detecting element, the second cable is drawn out with respect to the X-ray detecting element, and only one of the first and second connectors is connected to the X-ray detecting element. Therefore, it is possible to select a connector to be connected to the apparatus case so that the cable does not obstruct the imaging operation or the subject is not required to largely open the mouth. Consequently, an imaging operation can be easily conducted without giving the subject an unpleasant feeling.

In a sixth aspect of the invention, a dental X-ray image detecting apparatus comprises:

an X-ray detecting element for detecting an image produced by X-ray irradiation;

an apparatus case for housing the X-ray detecting element, capable of being inserted into a mouth;

a cable connected to the X-ray detecting element, for transmitting a signal from the X-ray detecting element to an external apparatus; and a cable connecting mechanism which enables a draw-out direction of the cable with respect to the X-ray detecting element, to be rotated and/or to be moved.

According to the sixth aspect of the invention, the draw-out direction of the cable is rotated or moved, and hence the cable can be drawn out at a desired rotation angle so that the cable does not obstruct the positioning of the detecting apparatus in the mouth or the subject is not required to largely open the mouth. Consequently, an imaging operation can be easily conducted without giving the subject an unpleasant feeling.

In a seventh aspect of the invention, the cable is provided with a buffer amplifier for amplifying the signal from the X-ray detecting element.

According to the seventh aspect of the invention, the impedance of the signal from the X-ray detecting element is lowered by the buffer amplifier, and hence the signal can be transmitted with an excellent S/N ratio even when the cable is long. This configuration is effective particularly in the case where the X-ray detecting element includes, for example, a CCD of high output impedance.

In an eighth aspect of the invention, an adaptor for dental X-ray image detecting apparatuses comprises:

an apparatus case for housing an X-ray detecting element for detecting an image produced by X-ray irradiation, capable of being inserted into a mouth, the adaptor being capable of being attached to and detached from the apparatus case, which is made of a soft and elastic material.

According to the eighth aspect of the invention, the adaptor for a dental X-ray image detecting apparatus is attached to and detached from the apparatus case. Therefore, when a plurality of different sorts of adaptors are prepared, for example, one of the adaptors which suits the shape of the dentition and the mouth interior can be selected to be attached to the apparatus case. In this configuration, an unpleasant feeling of the subject can be relieved. In addition, since the adaptor, which is contacted with the oral mucosa or teeth directly or indirectly via a disposable cover, can be made of an elastic and soft material, an unpleasant feeling of the subject can be relieved. Furthermore, since the adaptor is attached to the apparatus case, it is not necessary to configure the apparatus case with considering a contact with a mouth. Therefore, a case which is hardly broken and has high durability can be used as an apparatus case. In this way, the apparatus case and the adaptor can share the functions with each other.

BRIEF DESCRIPTION OF THE DRAWINGS

Other and further objects, features, and advantages of the invention will be more explicit from the following detailed description taken with reference to the drawings wherein:

FIGS. 15A to 15C are views showing modifications of the fifth embodiment of the invention;

DETAILED DESCRIPTION OF THE PREFERRED EMBODIMENTS

Figure 1:
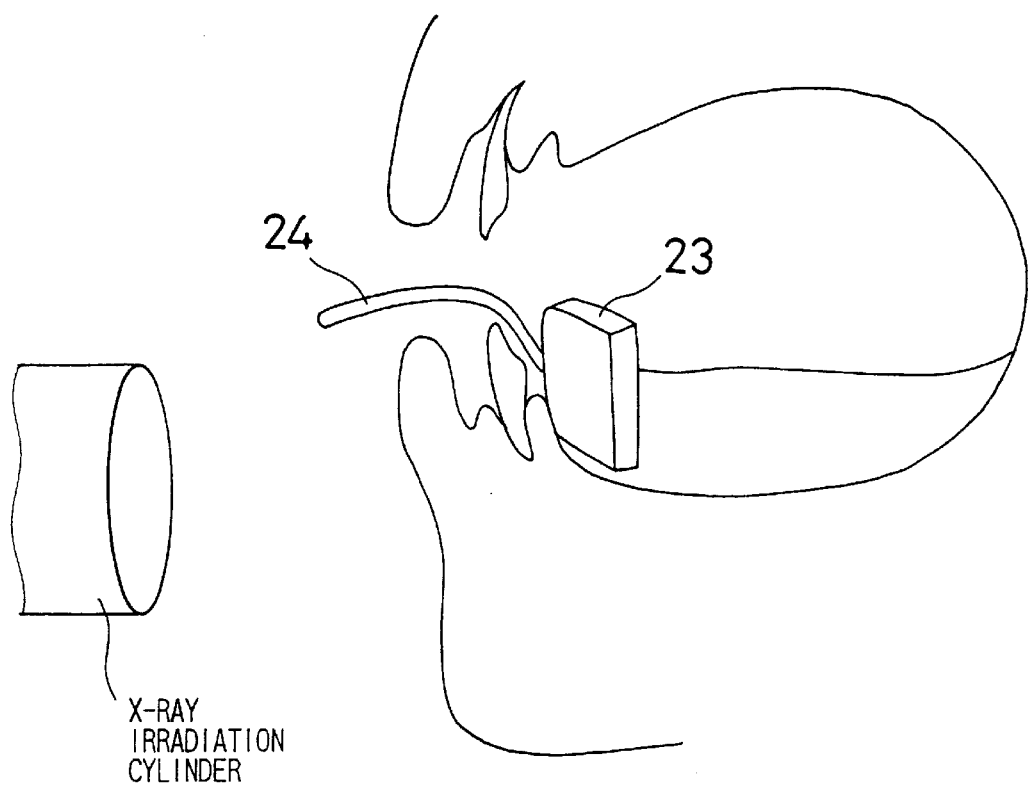
FIG. 1 is a partial perspective view illustrating an embodiment of the invention.

Now referring to the drawings, preferred embodiments of the invention are described below.

First Embodiment

FIG. 1 a perspective view illustrating embodiments of the invention.

Figure 2:
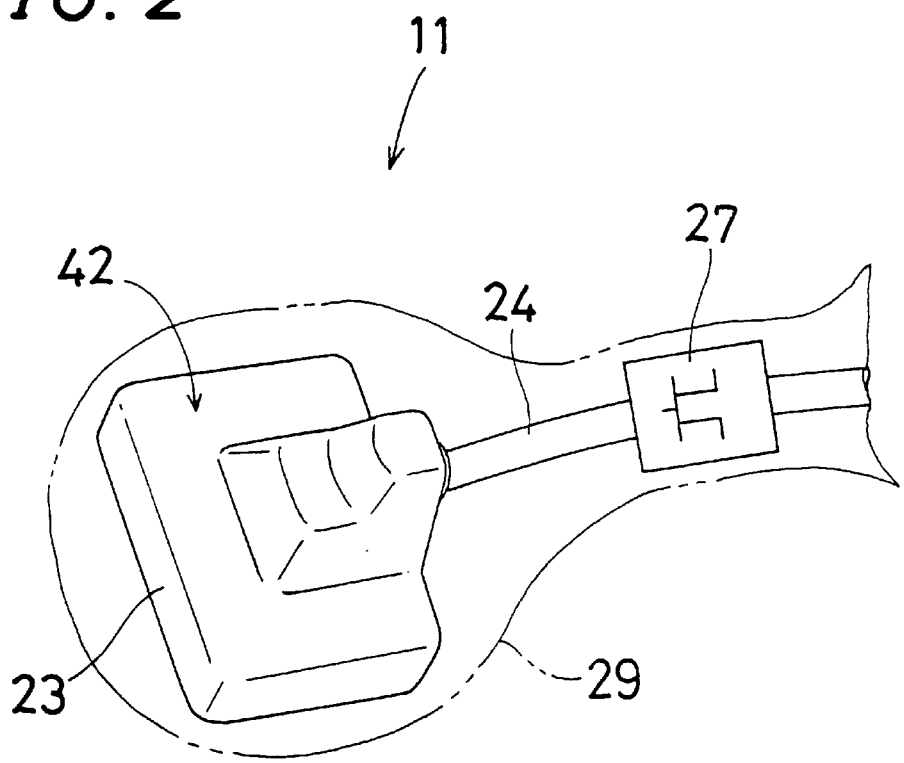
FIG. 2 is an external perspective view showing a first embodiment of the invention.
Figure 3A:
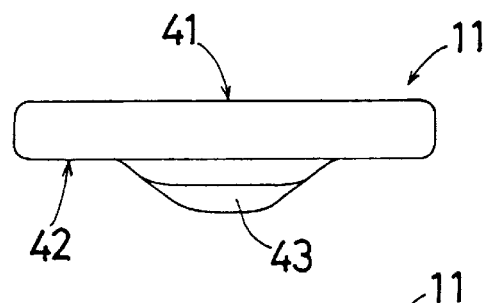
FIGS. 3A to 3D are front, plan, rear and side views showing the first embodiment of the invention.
Figure 3B:
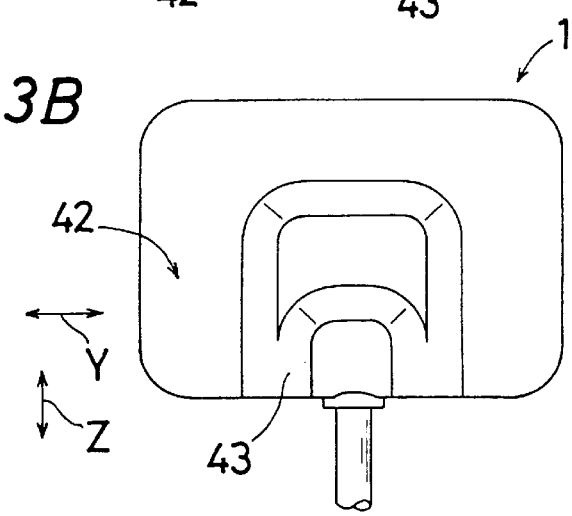
Figure 3D:
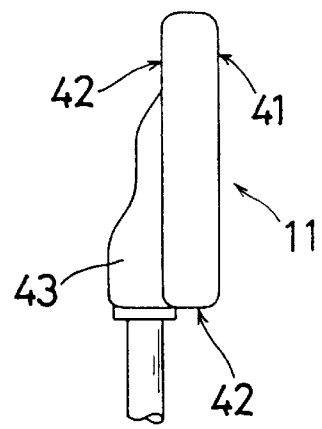
Figure 3C:
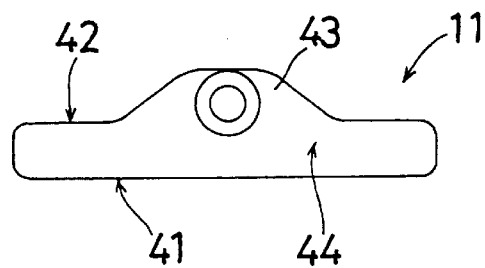
Figure 4:
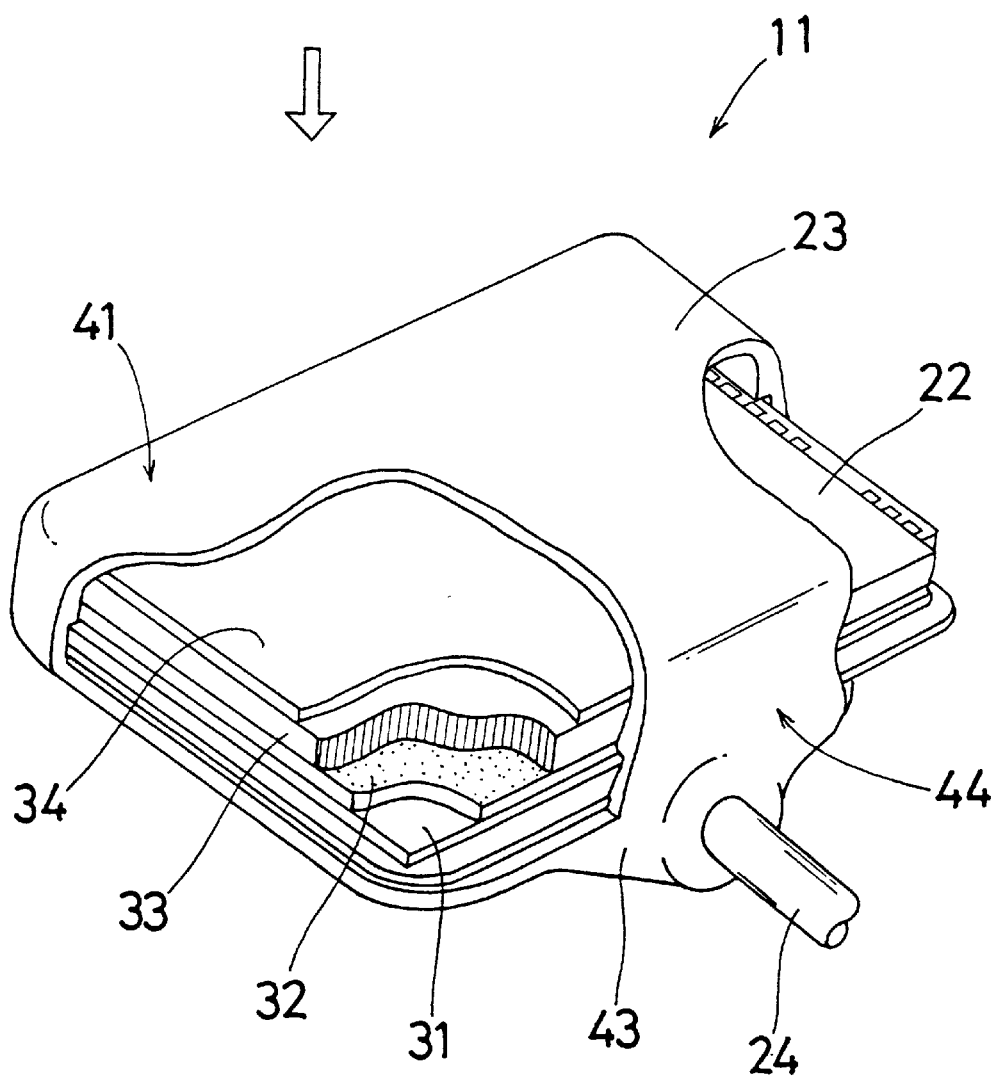
FIG. 4 is a view showing the internal structure of the first embodiment of the invention.

FIG. 2 is an external perspective view showing a first embodiment of the invention, FIGS. 3A to 3D are front, plan, rear and side views respectively showing the embodiment, and FIG. 4 is a view showing the internal structure of the embodiment. A dental X-ray image detecting apparatus 11 comprises an X-ray detecting element 22, an apparatus case 23 for housing the element, a cable 24, and a buffer amplifier 27.

Referring to FIG. 4, the X-ray detecting element 22 is illustrated below. The X-ray detecting element 22 is configured by stacking, on a substrate 31, a CCD (Charge Coupled Device) 32, an optical fiber plate 33, and a scintillator (fluorescent material) 34 in this sequence. An X-ray irradiated on an X-ray irradiation face 41 passes through the apparatus case 23 that is in a substantially rectangular parallelepiped shape like a matchbox thereby reaching the scintillator 34. The scintillator 34 converts the X-ray having reached the scintillator 34 into a visible light. The optical fiber plate 33 is configured by bundling optical fibers into a plate-like shape, and guides the visible light from the scintillator 34 to the CCD 32. The visible light from the optical fiber plate 33 is received and converted into an electric signal by the CCD 32.

The apparatus case 23 has a size which allows the apparatus case to be inserted into the mouth of the subject, and includes the X-ray irradiation face 41 on which an X-ray irradiates. Both the X-ray irradiation face 41 and a back face 42 which is on the opposite side of the irradiation face are formed to be substantially rectangular. A projected portion 43 is formed nearby one of the longer sides of the back face 42. The projected portion 43 is positioned in the vicinity of the center of the area nearby the longer side of the back face 42. In the projected portion 43, the cable 24 is connected, through a side face 44 adjacent to the back face 42 of the apparatus case 23, to the X-ray detecting element in the apparatus case 23. The X-ray detecting element 22 is incorporated in the region of the apparatus case 23 other than the projected portion 43. The apparatus case 23 has a size of, for example, 36 mm×26 mm×9 mm.

As described above, the cable 24 is connected to the projected portion 43 of the apparatus case 23, and drawn out from the apparatus case 23 in a direction Z. The direction Z is parallel with the X-ray irradiation face 41 and perpendicular to the longitudinal direction Y of the apparatus case 23. In the apparatus case 23, the cable 24 is electrically connected to the CCD 32, and the electric signal from the CCD 32 is transmitted through the cable 24 to the outside of the apparatus case 23. The provision of the projected portion 43 ensures a space for electrically connecting. The buffer amplifier 27 is disposed in a position which is on the cable 24 separated from the apparatus case 23 by about 10 cm. For the sake of simplicity, the buffer amplifier 27 is not shown in the drawings other than FIG. 2.

The dental X-ray image detecting apparatus 11 configured as shown above is used in a manner of that the apparatus case 23, the cable 24, and the buffer amplifier 27 are covered by a disposable cover 29. The use of the disposable cover 29 prevents entry of water into the apparatus and infection in the mouth.

The cable 24 may be drawn out in an oblique direction instead of a direction parallel to the X-ray irradiation face 41.

Second Embodiment

Figure 5:
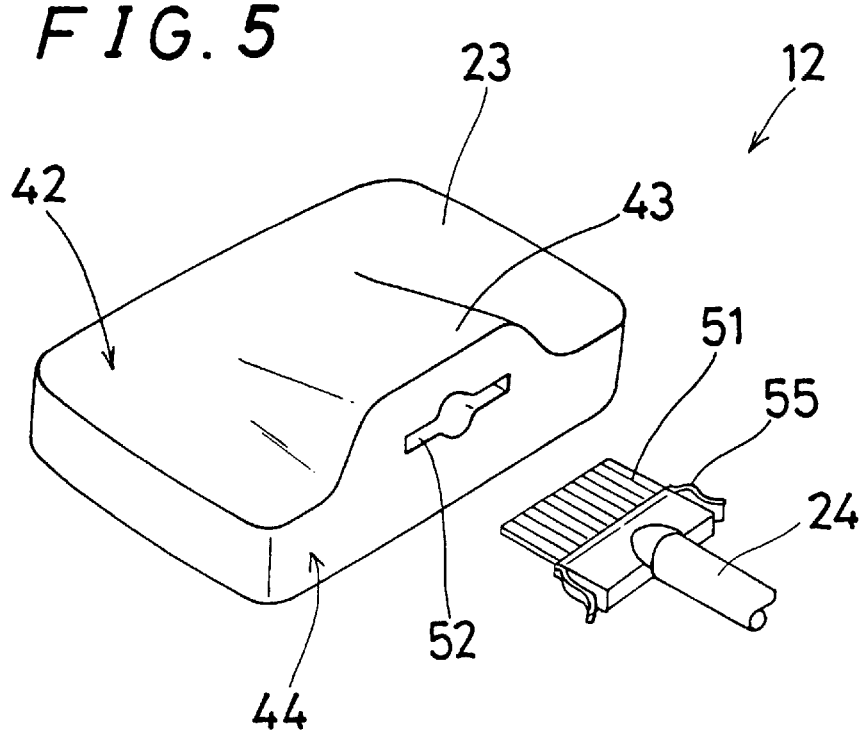
FIG. 5 is a perspective view showing a second embodiment of the invention.
Figure 6:
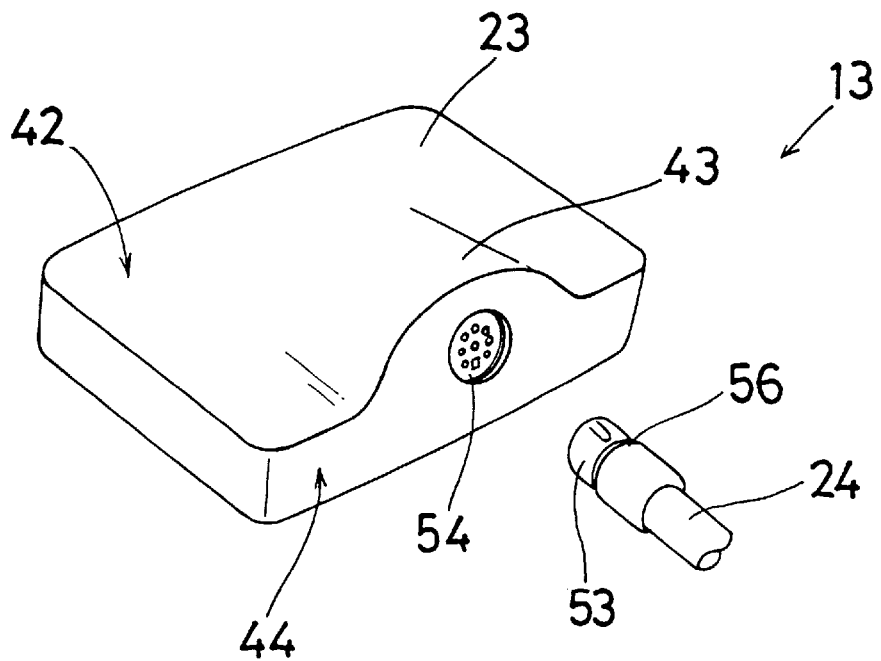
FIG. 6 is a perspective view showing the second embodiment of the invention.

FIGS. 5 and 6 are perspective views showing a second embodiment of the invention. A dental X-ray image detecting apparatus 12 is a partial modification of the dental X-ray image detecting apparatus 11 of FIG. 2. A flat convex connector 51 is formed at the tip end of the cable 24, and a concave connector 52 of the X-ray detecting element is formed on the side face 44 of the projected portion 43 of the apparatus case 23.

The flat convex connector 51 includes contacts which are made of an electrically conductive material, and lock levers 55 at both sides thereof. The lock levers 55 are made of an elastic material of resin or metal so as to have flexibility. The concave connector 52 has a shape which substantially corresponds to that of the flat convex connector 51, and includes contacts which are made of an electrically conductive material in the same manner as the flat convex connector 51.

The flat convex connector 51 is inserted into the concave connector 52 to be attached thereto. In the course of the attachment, the contacts of the connectors are contacted with each other thereby establishing an electrical connection between the connectors. The contacts of the flat convex connector 51 are electrically connected to the conductors inside the cable 24, and those of the concave connector 52 are electrically connected to the X-ray detecting element 22, with the result that the cable 24 is electrically connected to the X-ray detecting element 22. The inserted flat convex connector 51 is fixed to the concave connector 52 by the lock levers 55. When the lock levers 55 are pressed from both sides, the inserted flat convex connector 51 can be detached from the concave connector 52.

A dental X-ray image detecting apparatus 13 of FIG. 6 is a partial modification of the dental X-ray image detecting apparatus 12 of FIG. 5. The flat convex connector 51 is replaced with a cylindrical convex connector 53, and the concave connector 52 to a cylindrical concave connector 54. The cylindrical convex connector 53, which is circular in cross-section, includes a plurality of pins at the tip end, and a rubber ring 56 for watertight sealing. The cylindrical concave connector 54 includes insertion holes into which the pins of the cylindrical convex connector 53 are respectively inserted, and has a shape which substantially corresponds to that of the cylindrical convex connector 53. When the cylindrical convex connector 53 is inserted into the cylindrical concave connector 54, the pins are inserted into the respective insertion holes, thereby establishing an electrical connection between the connectors. During a period when the cylindrical convex connector 53 is inserted into the cylindrical concave connector 54, the connectors are fixed to each other so as to be hardly separated from each other, by the rubber ring 56. The fixation of the cylindrical convex connector 53 and the cylindrical concave connector 54 is not restricted to that based on the rubber ring 56, and may be realized by thread coupling or a fastening structure using a cap nut.

Third Embodiment

Figure 7:
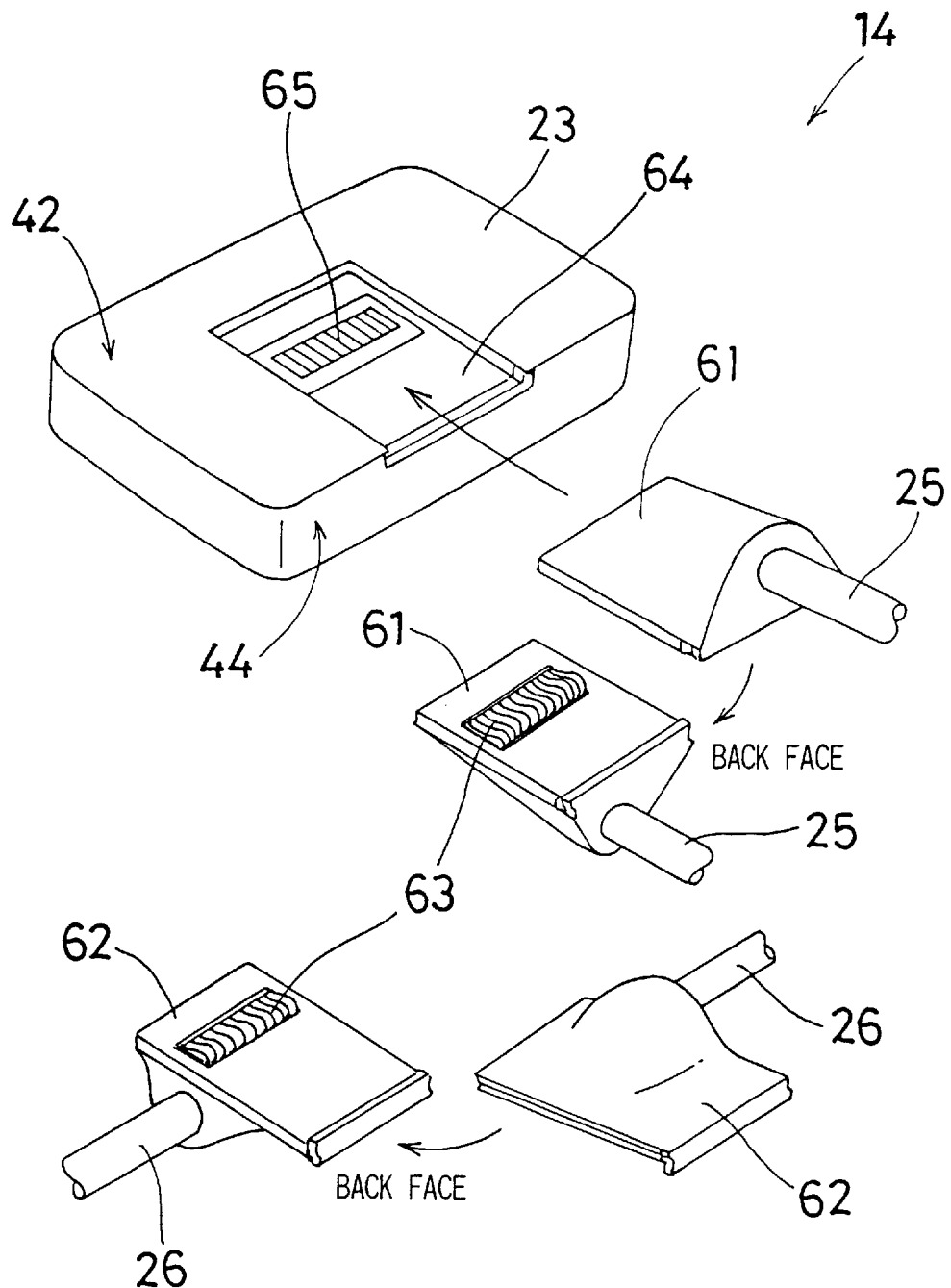
FIG. 7 is a perspective view showing a third embodiment of the invention.
Figure 8A:
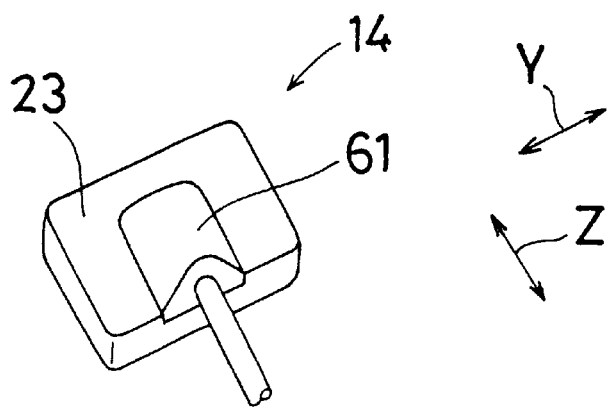
FIGS. 8A and 8B are perspective views showing the third embodiment of the invention.
Figure 8B:
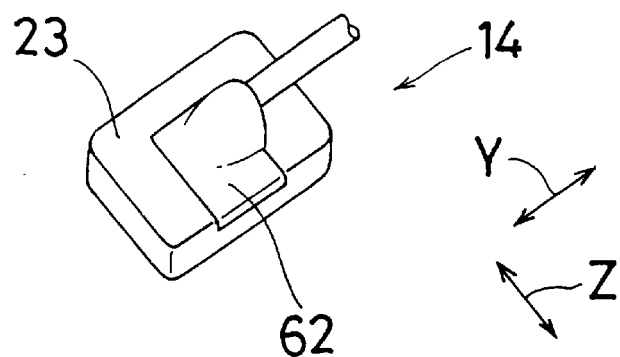

FIGS. 7, 8A and 8B are perspective views showing a third embodiment of the invention. A dental X-ray image detecting apparatus 14 is a partial modification of the dental X-ray image detecting apparatus 12 of FIG. 5. The projected portion 43 shown in FIG. 5 is removed away, the concave connector 52 is replaced with a concave connector 64, and the flat convex connector 51 is replaced with connectors of two kinds, i.e., first and second convex connectors 61 and 62. In accordance with these changes, the cable 24 is replaced with a first cable 25 connected to the first convex connector 61, and a second cable 26 connected to the second convex connector 62.

The concave connector 64 is formed on a position where the projected portion 43 is formed on the back face 42 of the apparatus case 23, in place thereof, and includes contacts 65 of the X-ray detecting element which are made of an electrically conductive material. Both the first and second convex connectors 61 and 62 are shaped into such a form that the convex connectors are slidably attached to the concave connector 64. Spring contacts 63 are disposed in portions where the convex connectors contact with the contacts 65 of the concave connector 64. Either one of the first and second convex connectors 61 and 62 is attached to the concave connector 64. As shown in FIG. 8A, when the first convex connector 61 is attached to the concave connector 64, the first cable 25 is drawn out in the direction Z perpendicular to the longitudinal direction of the apparatus case 23. As shown in FIG. 8B, when the second convex connector 62 is attached to the concave connector 64, the second cable 26 is drawn out in the direction Y which is parallel with the longitudinal direction of the apparatus case 23.

Fourth Embodiment

Figure 9:
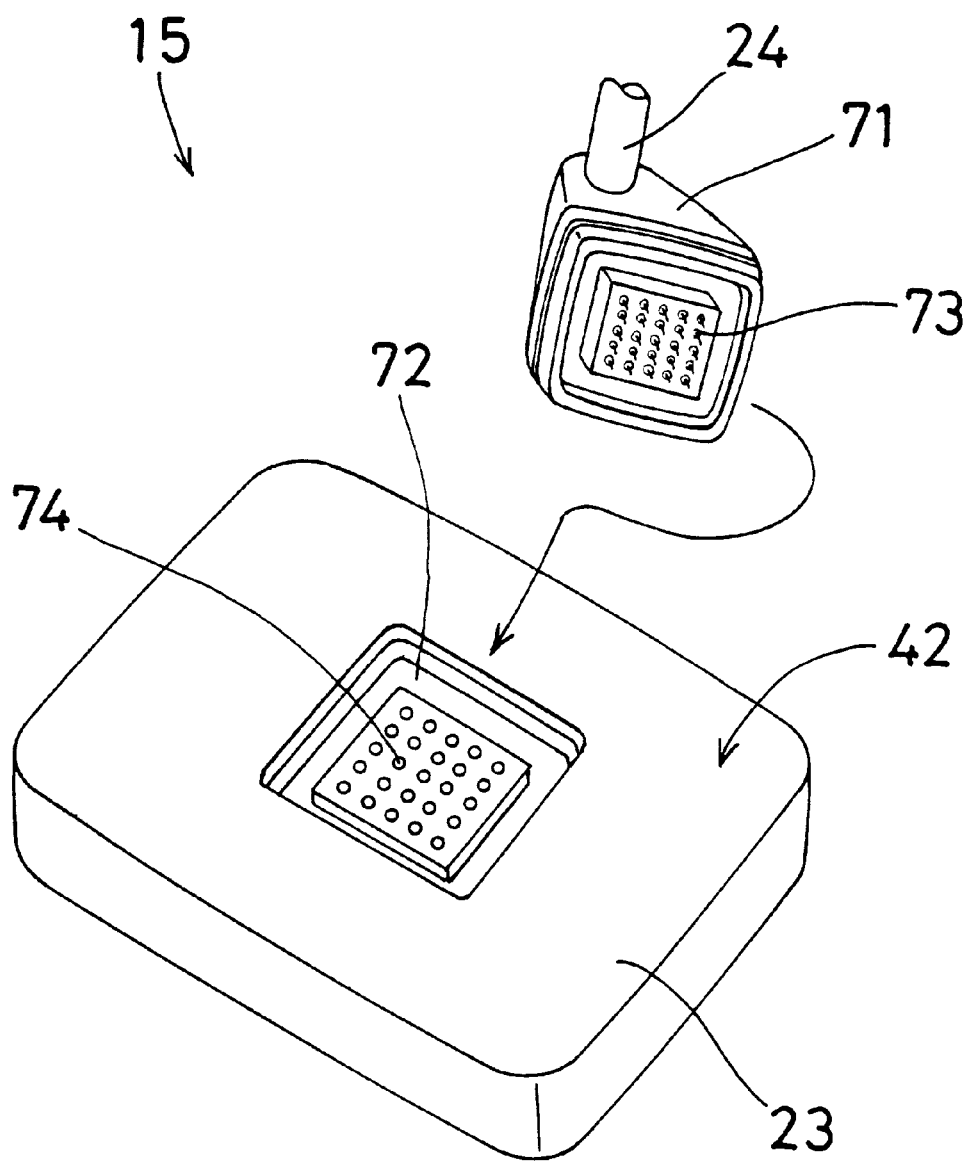
FIG. 9 is a perspective view showing a fourth embodiment of the invention.

FIG. 9 is a perspective view showing a fourth embodiment of the invention. A dental X-ray image detecting apparatus 15 is a partial modification of the dental X-ray image detecting apparatus 12 of FIG. 5. The flat convex connector 51 is replaced with a convex connector 71, and the concave connector 52 is replaced with a concave connector 72. The convex connector 71 and the concave connector 72 are used for constituting a PGA (Pin Grid Array). The respective faces of the connectors which are opposed to each other are formed to be square. A plurality of pins on the convex connector 71 are arranged so as to be rotationally symmetric by 90 degrees. Pin insertion holes on the concave connector 72 are also arranged in the same manner as the above. The concave connector 72 itself has a shape which substantially corresponds to that of the convex connector 71. Since the convex connector 71 can be attached to the concave connector 72 in one of four directions, the cable 24 can be drawn out in any one of the four directions. Alternatively, the attaching directions may be restricted to two directions which are mechanically perpendicular to each other. In the alternative, also the draw-out directions of the cable 24 are restricted to the two directions.

Fifth Embodiment

Figure 10:
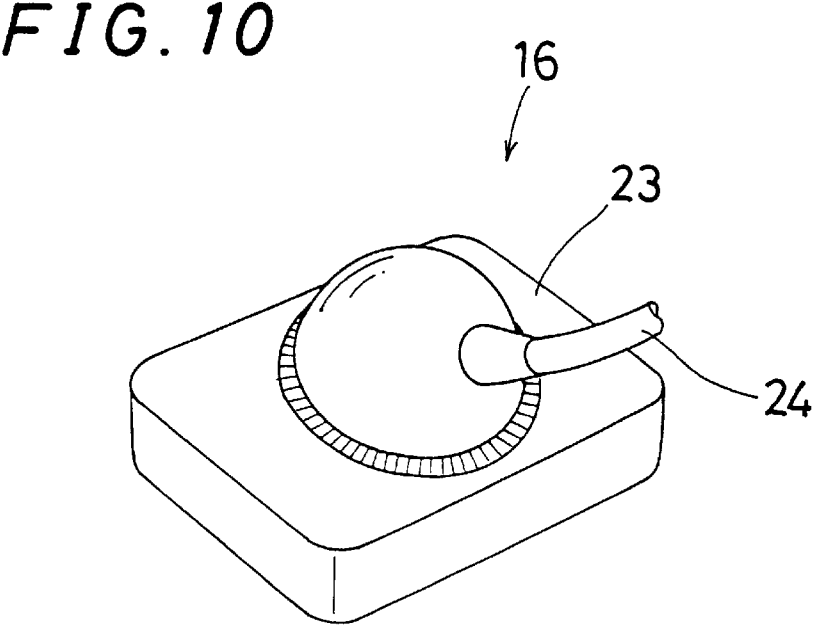
FIG. 10 is a perspective view showing a fifth embodiment of the invention.
Figure 11:
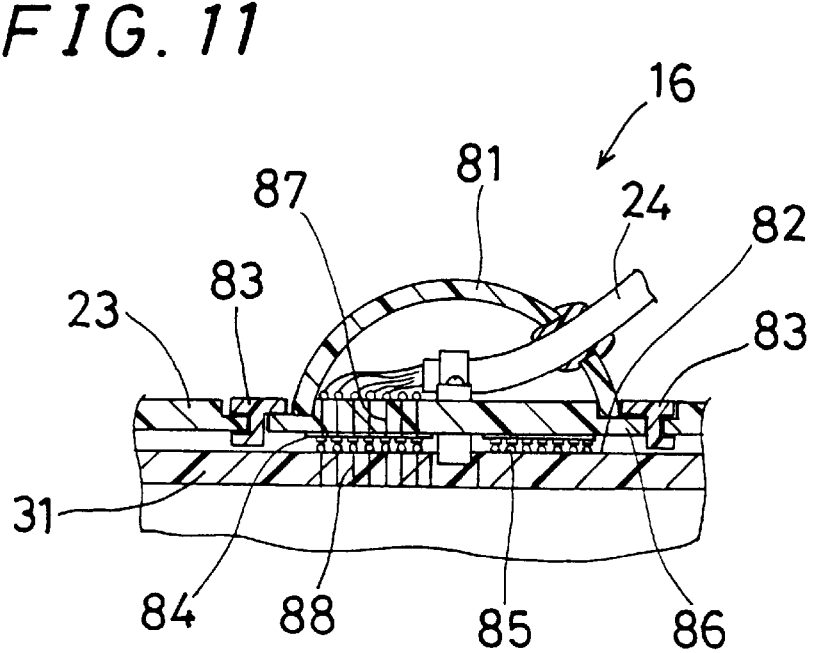
FIG. 11 is a section view showing the fifth embodiment of the invention.
Figure 12:
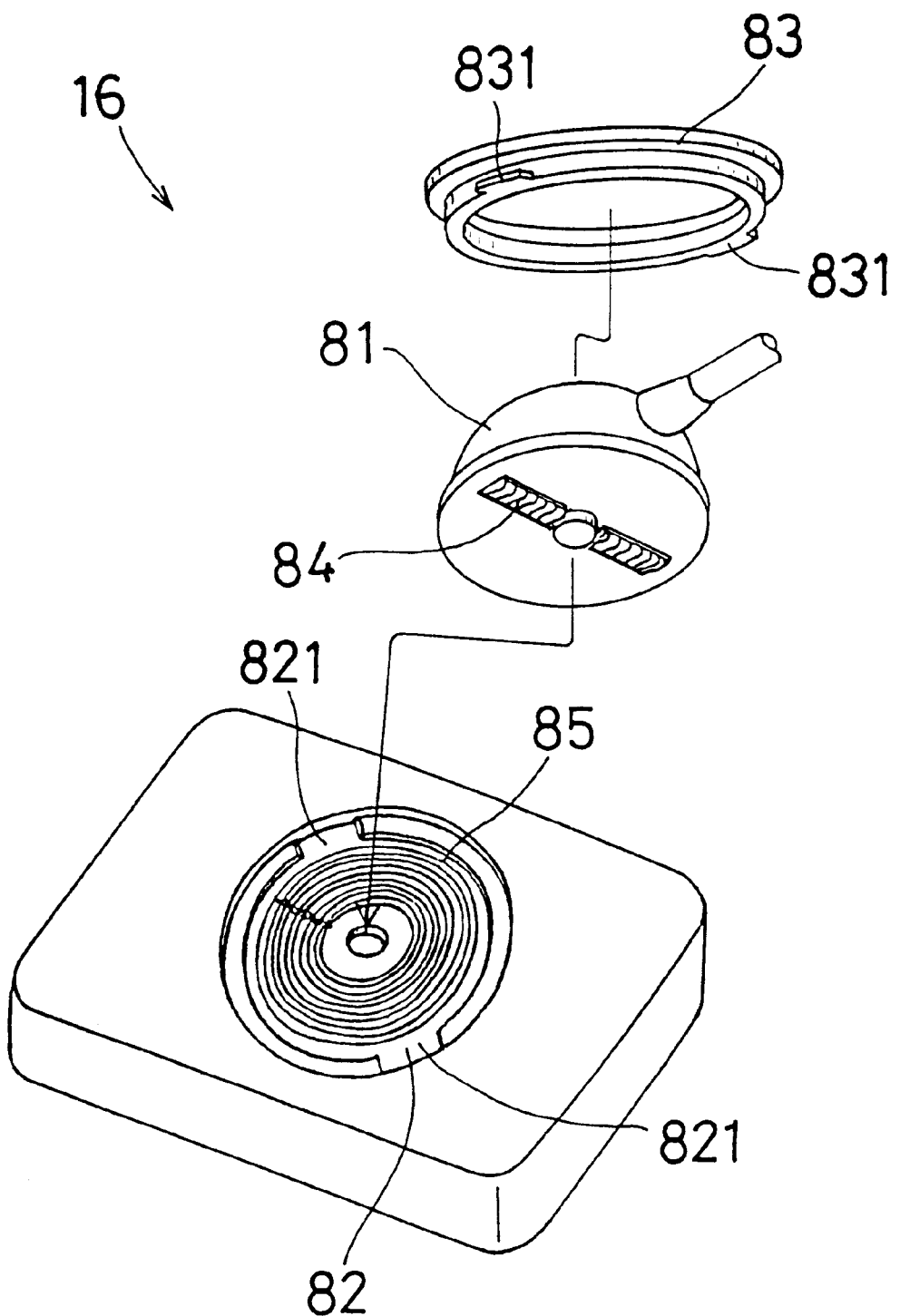
FIG. 12 is an exploded perspective view showing the fifth embodiment of the invention.

FIG. 10 is a perspective view showing a fifth embodiment of the invention, FIG. 11 is a section view of the embodiment, and FIG. 12 is an exploded perspective view of the embodiment. A dental X-ray image detecting apparatus 16 is a partial modification of the dental X-ray image detecting apparatus 15 of FIG. 9. The convex connector 71 is replaced with a convex connector 81, and the concave connector 72 is replaced with a concave connector 82.

The convex connector 81 is attached to the concave connector 82 of the X-ray detecting element, via a fixing ring 83. In the convex connector 81, a surface which is contacted with the concave connector 82 has a circular shape, and spring contacts 84 are formed thereon. Projections 831 of the fixing ring 83 are respectively fitted into cutaway portions 821 of the concave connector 82 and rotated, whereby the convex connector 81 is rotatively connected to the concave connector 82. Also in the concave connector 82, a surface which is contacted with the convex connector 81 has a circular shape, and concentric sliding contacts 85 are formed thereon. When the convex connector 81 is rotated with respect to the concave connector 82, the spring contacts 84 are kept to be contacted with the sliding contacts 85, during the rotation. The spring contacts 84 are electrically connected to the cable 24 via through holes 87 which are formed in an electrically insulating substrate 86 of the convex connector 81. On the other hand, the sliding contacts 85 are electrically connected to the CCD 32 via through holes 88 which are formed on the substrate 31.

Figures 13A, 13B:
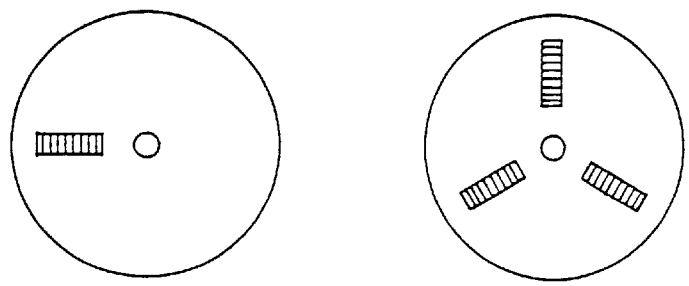
FIGS. 13A and 13B are views showing modifications of the fifth embodiment of the invention.
Figures 14A, 14B, 14C:
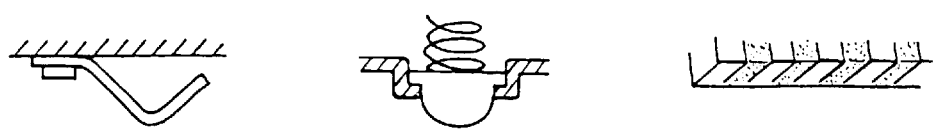
FIGS. 14A to 14C are views showing modifications of the fifth embodiment of the invention.
Figures 15A, 15C:
Figures 16A, 16B:
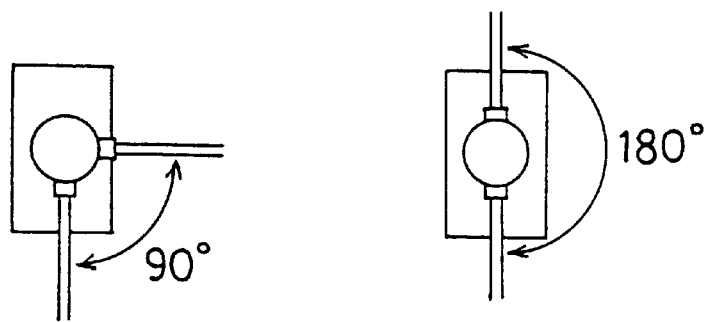
FIG. 16A and 16B are views showing modifications of the fifth embodiment of the invention.

FIGS. 13A to 16B are views showing modifications of the fifth embodiment. When disposing the spring contacts 84, the number of sets thereof is not restricted to two. As shown in FIGS. 13A and 13B, one set may be disposed, or three sets which are rotationally symmetric by 120 degrees may be disposed. Furthermore, the arrangement may be performed in any way, and four or more sets may be disposed. The shape of contacts is not restricted to that mentioned above. As shown in FIGS. 14A to 14C, each contact may be a plate spring, a dome-shaped spring, or electrically conductive rubber. The sliding contacts 85 are not required to be concentric circles which form one complete rotation. When the rotation angle of the convex connector 81 is mechanically limited, or as shown in FIGS. 13A and 13B, the number of sets of the spring contacts 84 is changed, each sliding contact can be configured to rotate by three quarters or one quarter of one complete rotation as shown in FIGS. 15A to 15C. In these cases, it is not required to route wiring to the back face of the substrate via through holes, and patterns can be routed along the substrate surface from areas where the circles of the sliding contacts are not formed. As shown in FIGS. 16A and 16B, the rotation angle of the convex connector 81 may be limited to 90 degrees or 180 degrees.

Sixth Embodiment

Figure 17:
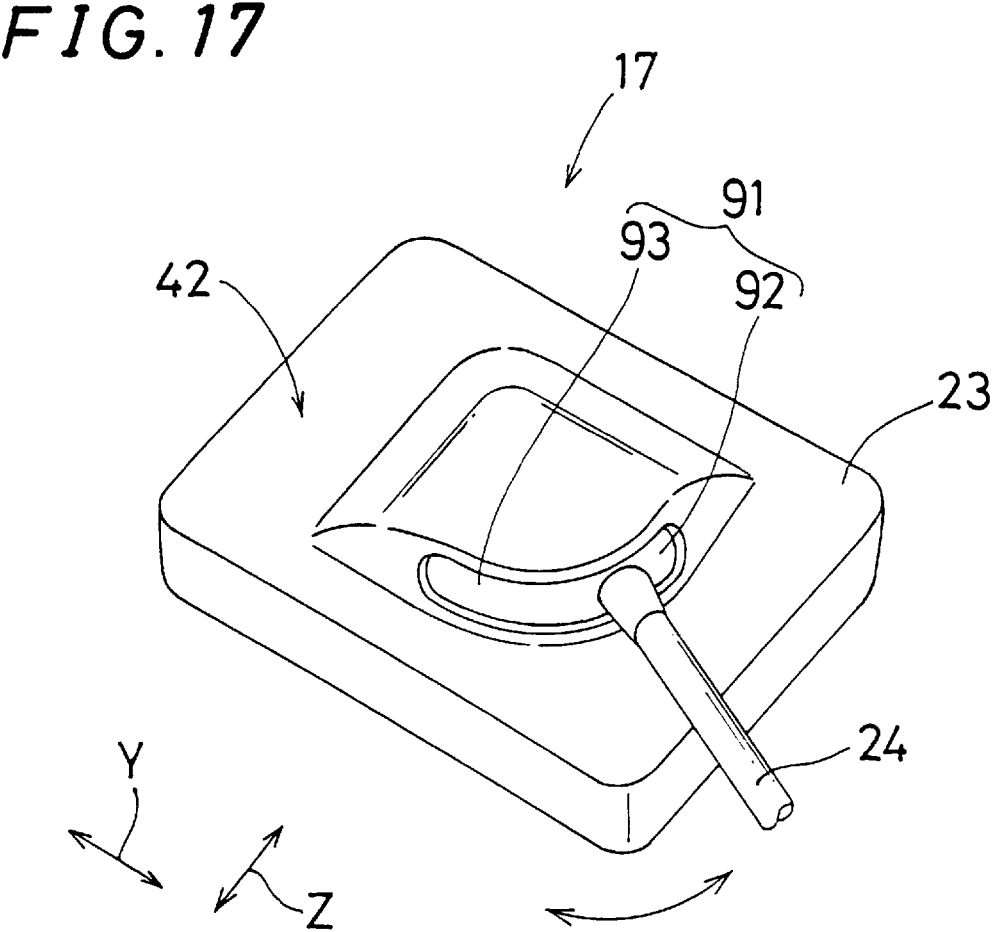
FIG. 17 is a perspective view showing a sixth embodiment of the invention.
Figures 18A, 18B:
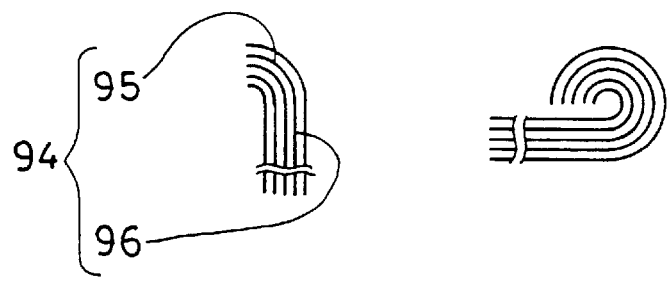
FIGS. 18A and 18B are views showing patterns of sliding contacts of the sixth embodiment of the invention.

FIG. 17 is a perspective view showing a sixth embodiment of the invention, and FIGS. 18A and 18B are views showing the patterns of sliding contacts of the embodiment. A dental X-ray image detecting apparatus 17 is a partial modification of the dental X-ray image detecting apparatus 16 of FIG. 10. As shown in FIG. 18A, the pattern of sliding contacts 94 of the dental X-ray image detecting apparatus 17 is configured by connecting parallel lines to portions in which a rotation of one-quarter of a concentric circle is conducted. A window 91 having an arcuate portion 92 and a linear portion 93 is formed on the back face 42 of the apparatus case 23, in accordance with the pattern of the sliding contacts 94. When the spring contacts of the convex connector are contacted with the concentric portion 95 of the sliding contacts 94, the cable 24 is drawn out through the arcuate portion 92 of the window 91. When the spring contacts are contacted with parallel-line portion 96 of the sliding contacts 94, the cable 24 is drawn out through the linear portion 93 of the window 91. In the arcuate portion 92, the draw-out direction of the cable 24 can be rotated by 90 degrees, and, in the linear portion 93, the draw-out position of the cable 24 can be moved in the direction Y.

As shown in FIG. 18B, in the pattern of the sliding contacts 94, the concentric portion 95 may be configured so that a rotation of three-quarter of a concentric circle is conducted. In this case, the arcuate portion 92 is widened to allow the draw-out direction of the cable 24 to be rotated by 270 degrees. Alternatively, the pattern of the sliding contacts 94 may be configured only by the parallel-line portion 96. In the alternative, the draw-out direction of the cable 24 is fixed to the direction Z. The moving direction and distance of the draw-out position of the cable 24 are not restricted.

Adaptor

Figure 19:
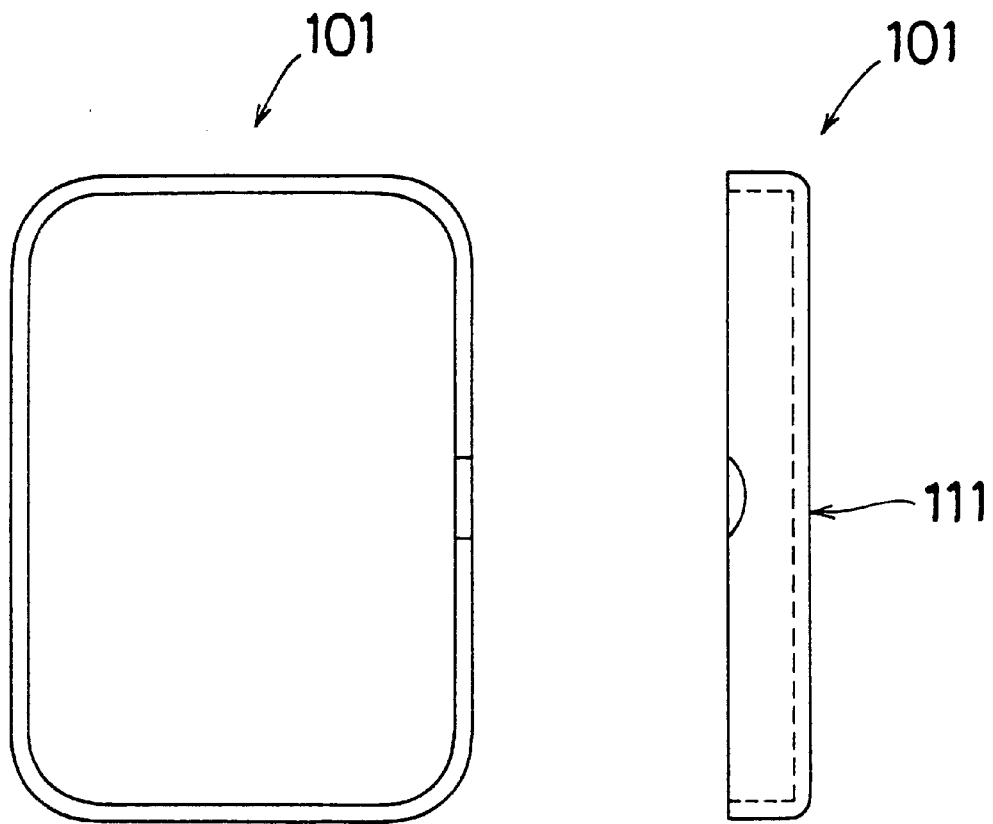
FIG. 19 is a set of three views showing an adaptor 101 for dental X-ray image detecting apparatuses 11 to 17.
Figure 19:
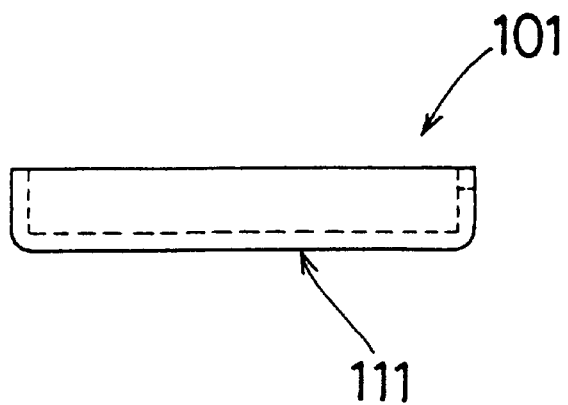
Figure 20:
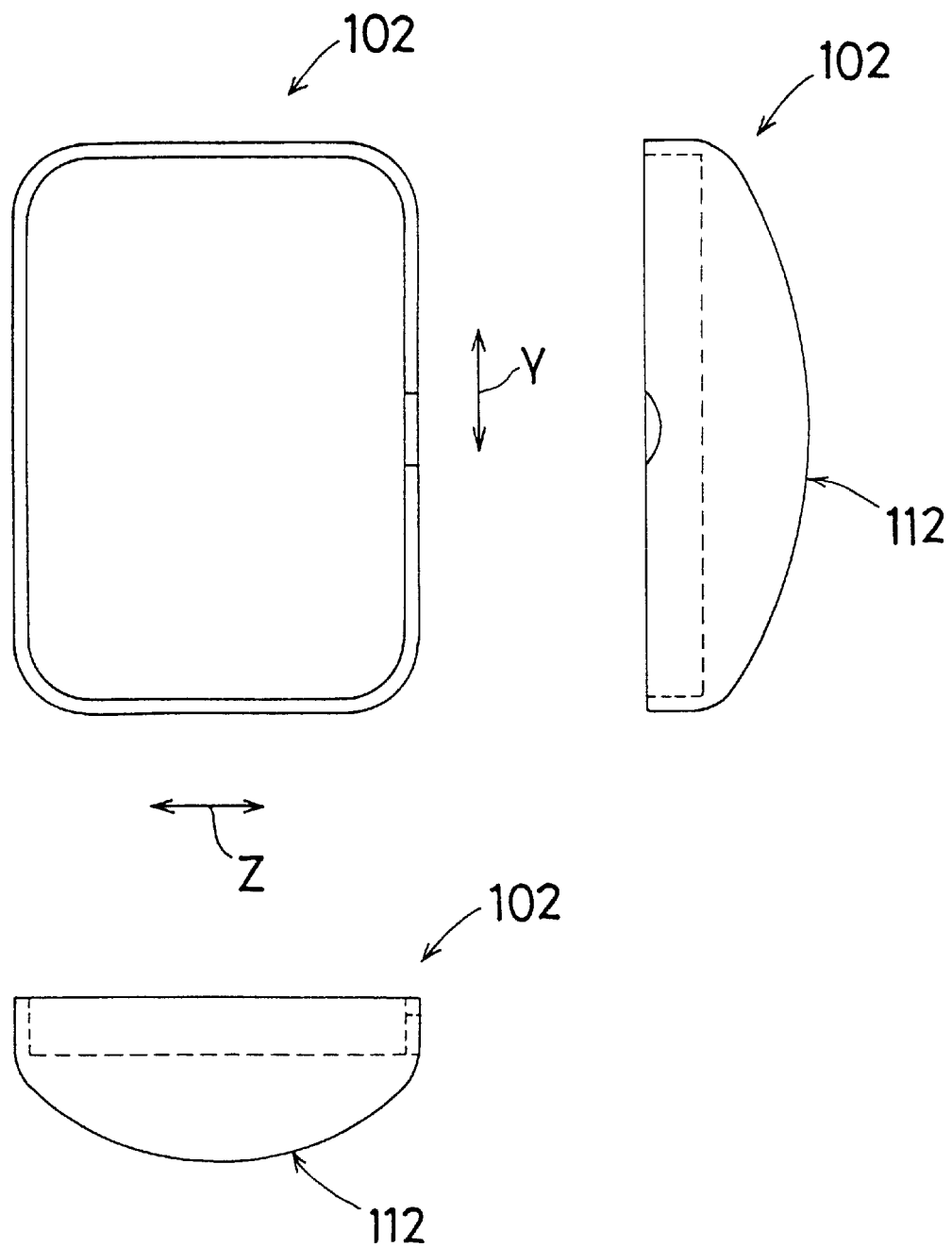
FIG. 20 is a set of three views showing an adaptor 102 for the dental X-ray image detecting apparatuses 11 to 17.
Figure 21:
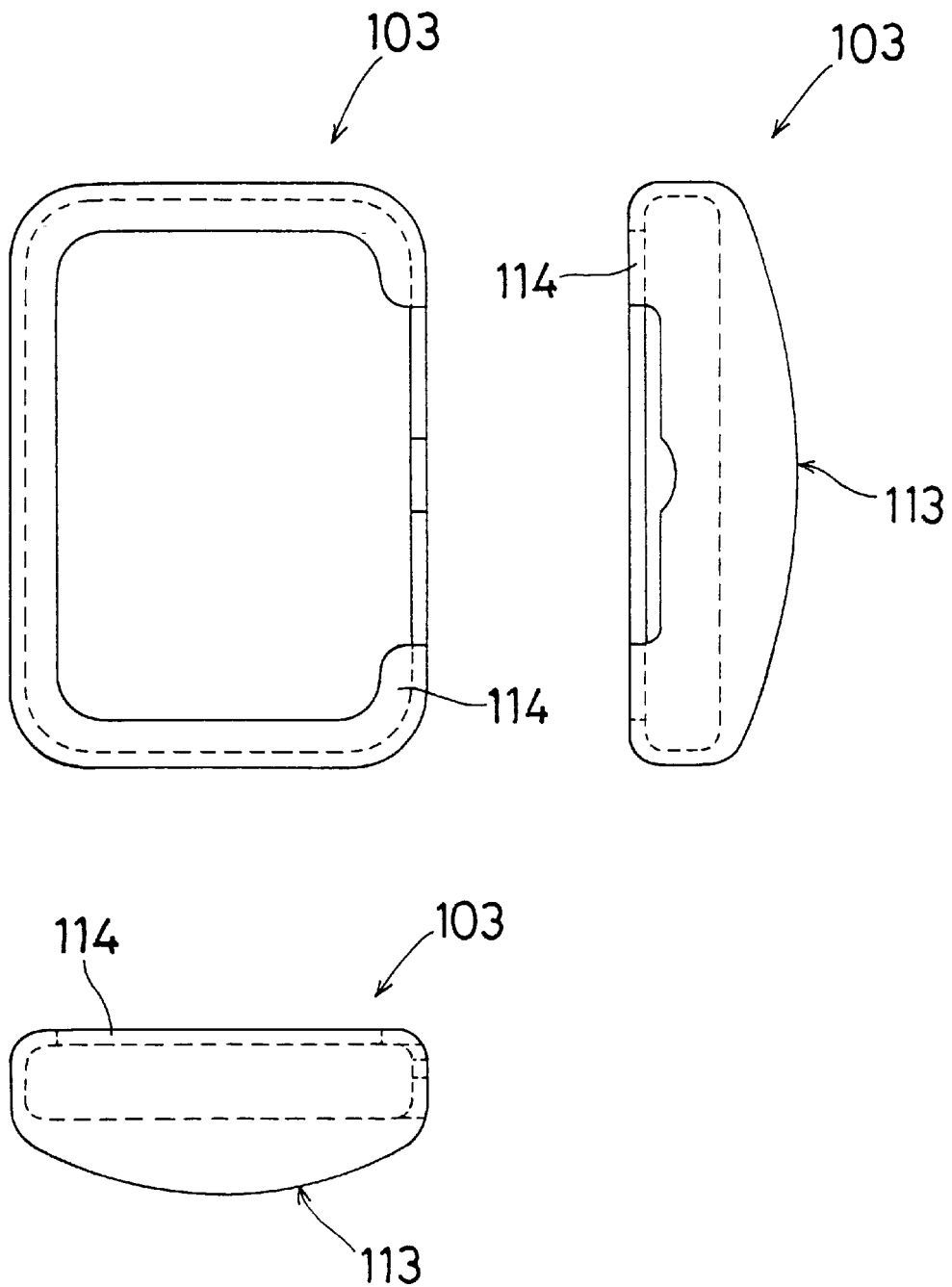
FIG. 21 is a set of three views showing an adaptor 103 for the dental X-ray image detecting apparatuses 11 to 17.

FIGS. 19 to 21 are sets of three views respectively showing adaptors 101 to 103 for the dental X-ray image detecting apparatuses 11 to 17. The adaptor 101 of FIG. 19 is made of a material having elasticity and softness, such as silicone rubber, polypropylene, or natural rubber, and has a shape which substantially corresponds to the outer shape of the apparatus case 23, so as to cover the X-ray irradiation face 41 and the side faces of the case. In the same manner as the X-ray irradiation face 41, an X-ray irradiation face 111 of the adaptor 101 which corresponds to the X-ray irradiation face 41 is flat.

In the same manner as the adaptor 101, the adaptor 102 of FIG. 20 is made of a soft and elastic synthetic resin and has a shape which substantially corresponds to the outer shape of the apparatus case 23, so as to cover the X-ray irradiation face 41 and the side faces of the case. An X-ray irradiation face 112 of the adaptor 102 is curved so that the center portion is swollen in both the directions Y and Z, thereby allowing the face to be fitted to the inside of the dentition.

In the same manner as the adaptor 101, the adaptor 103 of FIG. 21 is made of a soft and elastic synthetic resin and has a shape which substantially corresponds to the outer shape of the apparatus case 23, so as to cover the X-ray irradiation face 41 and the side faces of the case. In the same manner as the X-ray irradiation face 112 of the adaptor 102, an X-ray irradiation face 113 of the adaptor 103 is curved so that the center portion is swelled in both directions Y and Z, thereby allowing the face to be fitted to the inside of the dentition. The adaptor 103 has engaging portions 114 which cover the outer edge portion of the back face 42 of the apparatus case 23. The engagement of the apparatus case 23 is further enhanced by the engaging portions 114.

Figure 22:
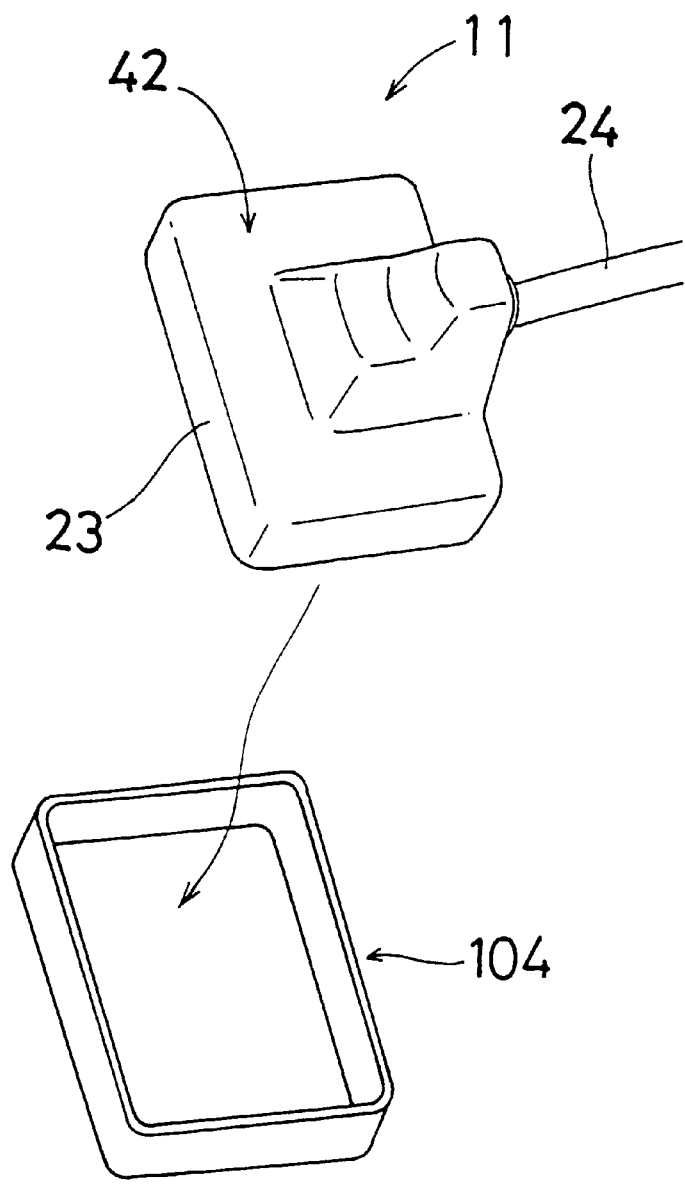
FIG. 22 is a perspective view showing an adaptor 104 for the dental X-ray image detecting apparatuses 11 to 17.
Figure 23A:
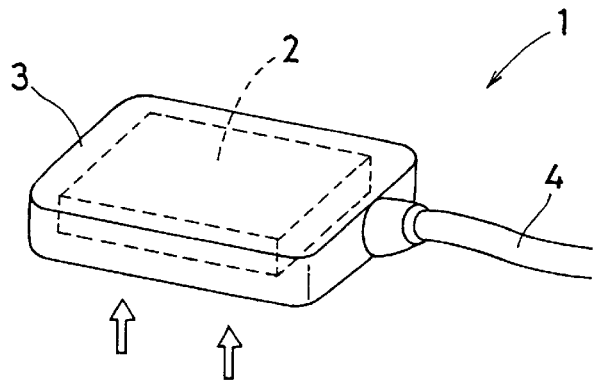
FIGS. 23A and 23B are perspective views showing a dental X-ray image detecting apparatus 1 of the prior art.
Figure 23B:
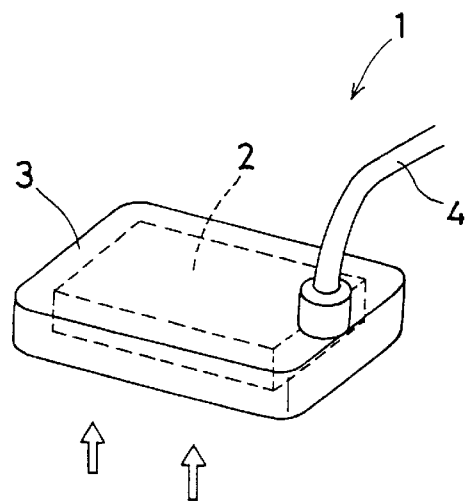
Figure 23C:
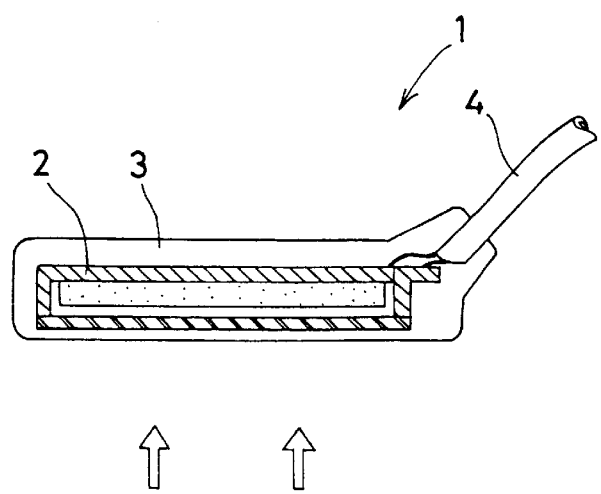
FIG. 23C is a section view of the apparatus 1.

FIG. 22 is a perspective view showing an adaptor 104 for the dental X-ray image detecting apparatuses 11 to 17. The adaptor 104 of FIG. 22 is made of a soft and elastic synthetic resin and covers only the side faces of the apparatus case 23 in the same manner as the adaptor 101.

Although the CCD 32 is used for the X-ray detecting element 22, the element may be an imaging element of another kind such as an MOS image sensor. The apparatus case 23 may be integrated with the cable 24 so as to be detachably attached to the X-ray detecting element. Also a configuration in which the apparatus case 23 is provided with an electric connector which is electrically connected to the X-ray detecting element and the cable is connected to the electric connector is in the scope of the invention.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A dental X-ray image detecting apparatus comprising:
   an apparatus case for housing an X-ray detecting element for detecting an image produced by X-ray irradiation, capable of being inserted into a mouth, and
   an adaptor for being attached to and detached from the apparatus case, said adaptor being made of a soft and elastic material.

2. A dental X-ray image detecting apparatus, comprising:
   an X-ray detecting element for detecting an image produced by X-ray irradiation;
   an apparatus case for housing the X-ray detecting element, capable of being inserted into a mouth;
   a cable connected to the X-ray detecting element, for transmitting a signal from the X-ray detecting element to an external apparatus;
   a cable attaching and detaching mechanism for attaching the cable to and detaching the cable from the X-ray detecting element; and
   a watertight seal member for the cable attaching and detaching mechanism.

3. A dental X-ray image detecting apparatus comprising:
   an X-ray detecting element for detecting an image produced by X-ray irradiation;
   an apparatus case for housing the X-ray detecting element, capable of being inserted into a mouth;
   a cable connected to the X-ray detecting element, for transferring a signal from the X-ray detecting element to an external apparatus; and
   a cable attaching and detaching mechanism for attaching the cable to and detaching the cable from the X-ray detecting element; and
   wherein the cable is provided with a buffer amplifier for amplifier for amplifying the signal from the X-ray detecting element.

4. A dental X-ray image detecting apparatus, comprising:
   an X-ray detecting element for detecting an image produced by X-ray irradiation;
   an apparatus case for housing the X-ray detecting element, capable of being inserted into a mouth;
   a cable connected to the X-ray detecting element, for transmitting a signal from the X-ray detecting element to an external apparatus; and
   a cable connecting mechanism for changing a draw-out direction and/or a draw-out position of the cable with respect to the X-ray detecting element, said connecting mechanism comprising a plurality of insertion pins and a plurality of insertion holes wherein said plurality of insertion pins and holes are arranged to be rotationally symmetric by 90°.

5. A dental X-ray image detecting apparatus, comprising:
   an X-ray detecting element for detecting an image produced by X-ray irradiation;
   an apparatus case for housing the X-ray detecting element, capable of being inserted into a mouth;
   first and second cables for transmitting a signal from the X-ray detecting element to an external apparatus; and
   first and second connectors disposed at ends of the first and second cables, respectively, which are selectively connected to the X-ray detecting element for providing different cable draw-out directions with respect to the X-ray detecting element; and wherein said first and second connectors are each provided with contacts arranged in the same way and said first and second cables have different draw-out directions relative to said contacts.

6. A dental X-ray image detecting apparatus, comprising:

an X-ray detecting element for detecting an image produced by X-ray irradiation;

an apparatus case for housing the X-ray detecting element, capable of being inserted into a mouth;

a cable connected to the X-ray detecting element, for transmitting a signal from the X-ray detecting element to an external apparatus; and a cable connecting mechanism which enables a draw-out direction of the cable with respect to the X-ray detecting element, to be rotated, said cable connecting mechanism comprising sliding contacts at least partially formed in concentric circles.

* * * * *